(12) United States Patent
Cueni et al.

(10) Patent No.: US 9,399,244 B2
(45) Date of Patent: Jul. 26, 2016

(54) LABORATORY FERMENTER WITH CLEANING DEVICE

(71) Applicant: Infors AG, Bottmingen (CH)

(72) Inventors: Dieter Cueni, Zwingen (CH); Daniel Egger, Binningen (CH)

(73) Assignee: Infors AG, Bottmingen (CH)

( * ) Notice: Subject to any disclaimer, the term of this patent is extended or adjusted under 35 U.S.C. 154(b) by 359 days.

(21) Appl. No.: 13/895,950

(22) Filed: May 16, 2013

(65) Prior Publication Data

US 2014/0338707 A1 Nov. 20, 2014

(51) Int. Cl.
*B08B 9/08* (2006.01)
*C12M 1/00* (2006.01)

(52) U.S. Cl.
CPC . *B08B 9/08* (2013.01); *C12M 39/00* (2013.01)

(58) Field of Classification Search
CPC .............................. C12M 39/00; B01L 99/00
See application file for complete search history.

(56) References Cited

U.S. PATENT DOCUMENTS 5,213,981 A * 5/1993 Sei .............................. 435/286.4
2010/0317102 A1 * 12/2010 Suzuki et al. .................. 435/366

* cited by examiner

*Primary Examiner* — Jason Ko
*Assistant Examiner* — Spencer Bell
(74) *Attorney, Agent, or Firm* — Crowell & Moring LLP

(57) ABSTRACT

A cleaning device for a laboratory fermenter for growing microorganisms is provided. The laboratory fermenter to be cleaned has a gas supply connection connected to a line reaching into the fermenter's nutrient solution, an exhaust connection to the gas space over the nutrient solution, and a withdrawal connection leading to the fermenter's deepest point. The cleaning device includes three cleaning connections, an immersion pipe connection and two gas connections. Flow in each gas connection is controlled via intermediate switch valves having a cleaning start position and a cleaning end position. The cleaning connections are connected via hose lines to hose pinch control valves, a hose pinch pump, at least one filter. A cleaning control manages the cleaning process by controlling flow from and/or to an air connection, a water connection and a waste water connection. The cleaning controller may also control introduction of acids and/or bases.

2 Claims, 2 Drawing Sheets

LABORATORY FERMENTER WITH CLEANING DEVICE

BACKGROUND AND SUMMARY OF THE INVENTION

The invention concerns a generic cleaning device for a laboratory fermenter according to the preamble of the main claim, namely such a device for a laboratory fermenter for growing microorganisms such as bacterial or fungal cultures or cell cultures, where the laboratory fermenter is provided with a gas supply connection which is called a sparger and which is connected to a line reaching into the nutrient solution, with an exhaust connection leading to the gas space located over the nutrient solution and in given cases connected to an exhaust cooler on the Outer side of the laboratory fermenter, and with a withdrawal connection for the nutrient solution or cleaning fluid and leading to the lowest point in the fermenter. Along with this the laboratory fermenter can comprise additional components known per se, such as a stirring mechanism, measurement sensors, heating, and the supply of base, acid, AF, feed, etc. via pumps and push valves as well as air supplies of less than 1, preferably 0.5 bar.

Such a cleaning device for parts of laboratory fermenter with a holding capacity up to ca. 30 liters is known per se as an autoclave.

In order to be able to clean this laboratory fermenter after it has been used, it is necessary to disassemble it and first clean the smaller parts, then place them in an autoclave, and finally autoclave them. After the sterilization in this manner has been completed the parts must be re-assembled in the sterile state so that the laboratory fermenter is once again ready for use. This known type of churning requires more than an entire day and moreover must be done by a technician in a chemical laboratory. Thus the cleaning of laboratory fermenters consumes considerable resources.

The object of the invention is thus to provide a laboratory fermenter cleaning device which consumes fewer resources in its operation.

The inventive laboratory fermenter cleaning device includes three cleaning connections, namely an immersion pipe connection and two gas connections, each gas connection is conducted to an intermediate switch valve having an outlet, each intermediate switch valve has two switch positions, namely a cleaning start position letting the gas connection open to the outlet and a cleaning end position closing this connection, the cleaning connections are connected via lines to control valves, a pump, a filter, and by a cleaning control which manages the cleaning process to an air connection, a water connection, and a waste water connection, where the lines are formed as hose lines, the valves as hose pinch valves, and the pump as a hose pinch pump.

The cleaning device transportable according to the invention is connected by its immersion pipe connection to the withdrawal connection and by its two gas connections, via the intermediate valves in the cleaning start position, to the gas supply connection and the exhaust connection of the laboratory fermenter to be cleaned. After introducing a base, e.g., sodium hydroxide solution and/or water, into the laboratory fermenter for the purpose of cleaning it, in that cleaning process the mixture, in given cases reversing its flow direction and in given, cases adding water from the water connection, is circulated for a sufficiently long time, then neutralized by adding acid, e.g., phosphoric acid, and finally, by adding air into the gas space via the withdrawal connection of the laboratory fermenter, transported to the immersion pipe connection and ultimately to the waste water connection which can be connected to waste water tank (a so-called kill tank). After the end of the cleaning process all the hose connections to the laboratory fermenter can be separated and in given cases closed at the cleaning connections, leaving the intermediate valves still in their cleaning start position on the laboratory fermenter, which is then completely cleaned and ready for a new fermentation cycle without being disassembled into parts and autoclaving of the same being necessary. The cleaning device according to the invention can also be provided internally with a water tank and also a waste water tank as well as an electric battery for the pump and the cleaning control. It is also possible that, external tanks and the electric AC power supply may be used instead of internal power and waste water features.

So that the cleaning work is not shifted from the laboratory fermenter to the cleaning device according to the invention, all and thus all interrelated hose lines are separated in the manner of a hose line tree as a hose line set from the hose pinch valves and the hose pinch pump after being used several times and replaced with a hose line set which is new and clean, but not necessarily sterile because the hose line set is cleaned and sterilized by the base rinsed through initially wherewith the cleaning device can also be used once again for the next cleaning process.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 2:
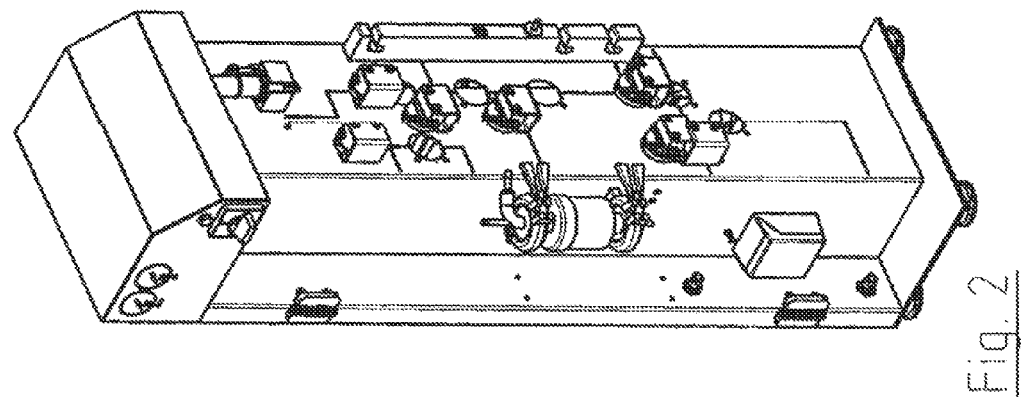
FIG. 2 shows the cleaning device according to FIG. 1.
Figure 1:
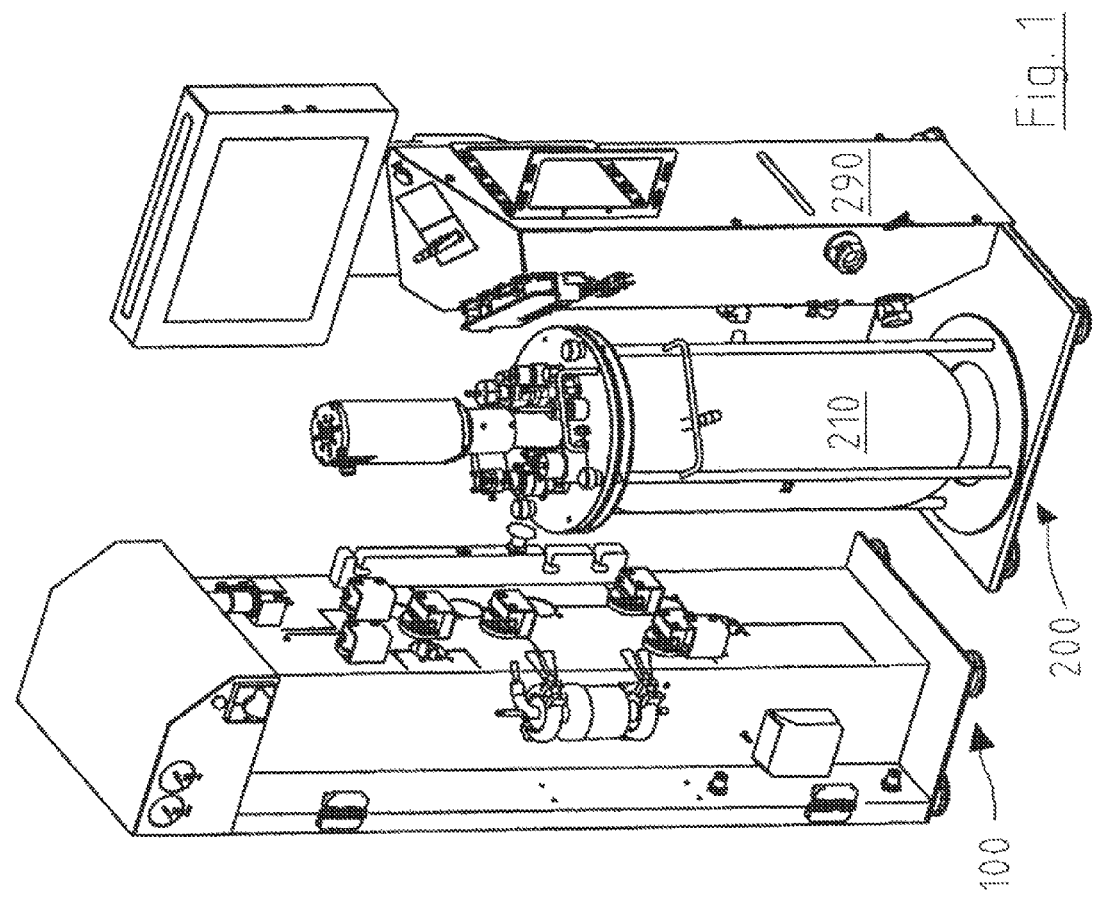
FIG. 1 shows a cleaning device as well as a laboratory fermenter with a control unit in accordance with the present invention in perspective representation.

The cleaning device 100 for a fermenter 200 for growing bacterial or fungal cultures is represented in schematic representation in FIG. 1. The fermenter 200 comprises a cleaning control 290 and the actual laboratory fermenter 210. This can preferably be provided on its cover with additional components known per se such as a stirring mechanism next to the motor M, measurement sensors, heating, and the supply of base, acid, AF, feed etc., via pumps P and push valves as well as air supplies of less than 1, preferably 0.5 bar which in this connection are not of greater interest and thus are not described in more detail. Furthermore, via a CIP/SIP push valve the laboratory fermenter 210 can be supplied by a pump P3 located in a part 190 of the cleaning device 100 with a sodium hydroxide solution as a base and by a pump P2 with phosphoric acid as an acid for the purposes of or subsequent neutralization.

Figure 3:
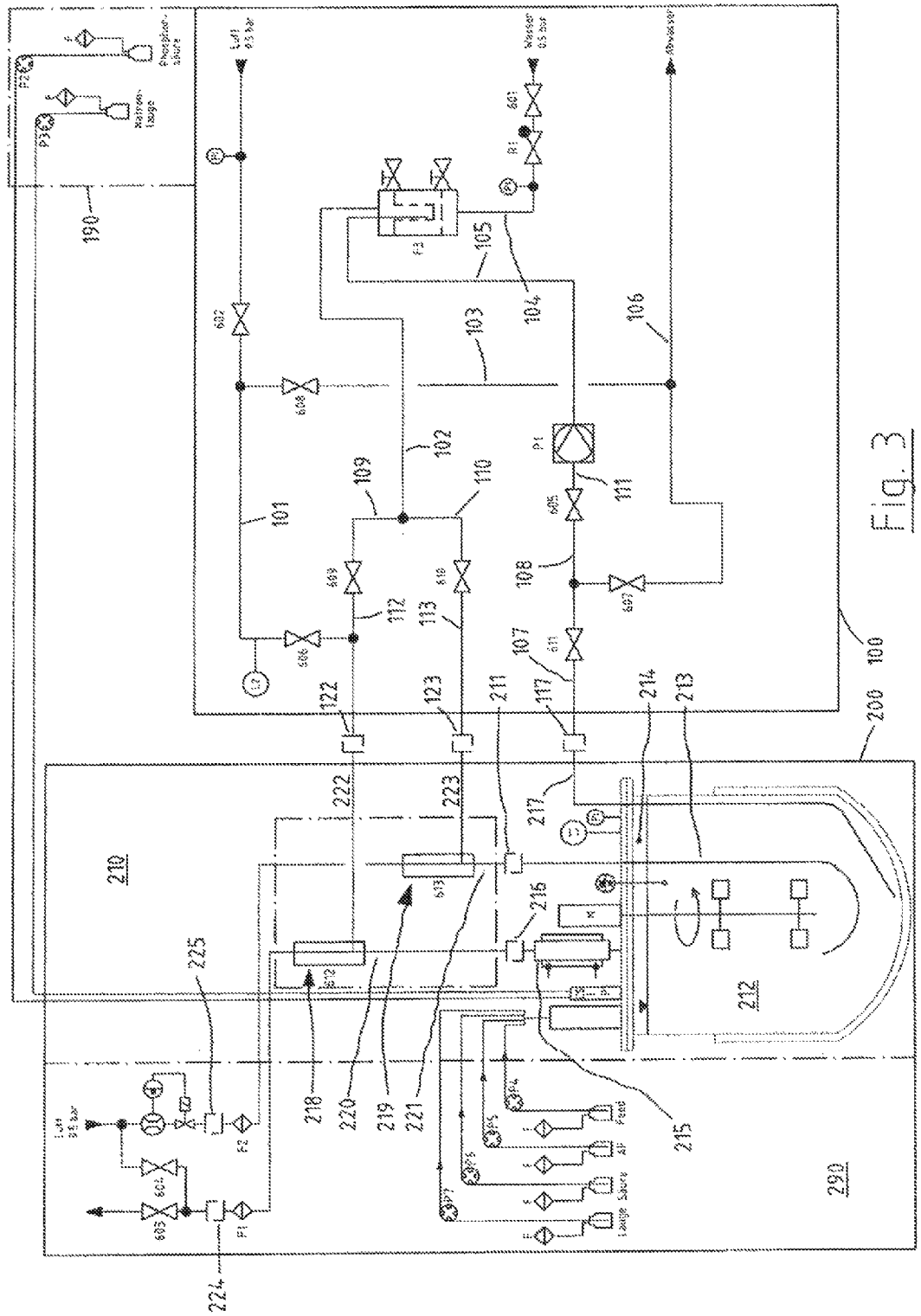
FIG. 3 shows a configuration diagram for the cleaning device and the laboratory fermenter according to FIG. 1.

Furthermore, as FIG. 3 shows, the laboratory fermenter 210 comprises a gas supply connection 211 called a "sparger" and connected to a line 213 reaching into the nutrient solution 212, an exhaust connection 216 leading to the gas space 214 located over the nutrient solution 212 and in given cases connected to an exhaust cooler 215 on the outer side of the laboratory fermenter 210, and a withdrawal connection 217 for the nutrient solution and leading to the lowest point in the laboratory fermenter 210. The gas supply connection 211 and the exhaust gas connection 216 are each conducted to an intermediate switch valve 218, 210 which is formed as a 3/2 valve, has an outlet 220, 221, has two switch settings, and whose outlet in one switch setting, namely the cleaning start position, is connected to cleaning connections 222, 223 or in the other switch setting, namely the cleaning end position or operational setting of the laboratory fermenter, is only connected to connections 224, 225 of the cleaning control 290 during operation.

The cleaning device 100 is connected to valves 601, 602 and 605, 610, to circulating pump P1, a filter F3, and by a not represented cleaning control, manages a cleaning process to an air connection, a water connection, and a waste water connection where after introducing a sodium hydroxide solution and/or water from the part 190 into the laboratory fermenter 210 for the purpose of cleaning it the cleaning control during that cleaning process circulates the mixture for a long enough time and in cases reversing the direction of flow, then by adding phosphoric acid as acid neutralizes it, and finally by adding air into the gas space 214 over the withdrawal connection 217 of the laboratory fermenter transports it to an immersion pipe connection 117 of the cleaning device 100 and ultimately transports it to the waste water connection which can be connected to a so-called kill tank.

For temporarily connecting to the laboratory fermenter 210 for the purpose of cleaning it the cleaning device 100 comprises three cleaning connections 117, 122, 123, namely an immersion pipe connection 117 and two gas connections 122, 123 both of the latter being conducted to the intermediate switch valves 218, 219 flaying the outlets 220, 221. After performing the cleaning the cleaning device 100 is separated at its three cleaning connections 117, 122, 123 from the laboratory fermenter 210 and if necessary sealed with stoppers while the intermediate valves 218, 219 remain on the laboratory fermenter 210, which is then ready to be used again.

Finally all the lines 101-113 in the cleaning device 100 are formed as hose lines which are interrelated and connected to one another, the valves 601, 602 and 605, 610 are formed as hose pinch valves, and the circulating pump P1 is formed as a hose pinch pump. Due to this the cleaning work is not shifted from the laboratory fermenter 210 to the cleaning device 100 according to the invention since all its hose lines and thus all its interrelated hose lines can be removed in the manner of a hose line tree as a hose line set from the hose pinch valves and the hose pinch, pump after being used several times and replaced with a new, clean hose line set, wherewith the cleaning device is also once more ready for use in the next cleaning process.

The foregoing disclosure has been set forth merely to illustrate the invention, and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A laboratory fermenter for growing microorganisms, comprising:
   a laboratory fermenter fermenting tank;
   a gas supply connection of the laboratory fermenter communicating with the fermenting tank;
   a gas supply line of the laboratory fermenter communicating with the fermenting tank, the gas supply line operatively connected to the gas supply connection;
   an exhaust connection of the laboratory fermenter communicating with a gas space within the fermenting tank;
   a withdrawal connection of the laboratory fermenter communicating with a lowest point of fermenting tank;
   a first intermediate switch valve communicating with the exhaust connection and the fermenting tank;
   a second intermediate switch valve communicating with the gas supply line and the fermenting tank;
   a cleaning device, the cleaning device having at least three cleaning connections including
      an immersion pipe cleaning connection operably connectable to the laboratory fermenter withdrawal connection,
      a first cleaning connection operably connectable to the laboratory fermenter exhaust connection via the first intermediate switch valve, and
      a second cleaning connection operably connectable to the laboratory fermenter gas supply connection via the second intermediate switch valve;
   a cleaning device circulating pump downstream of the immersion pipe cleaning connection and upstream of the first and second cleaning connections;
   at least one filter downstream of the immersion pipe cleaning connection and upstream of the first and second cleaning connections;
   control valves arranged to control flow of at least one cleaning media between the immersion pipe cleaning connection and the first and second cleaning connections; and
   a cleaning controller;
   wherein
      when each intermediate switch valve is in a respective cleaning start position the respective cleaning connection communicates with the fermenting tank, and when in a respective cleaning end position the respective cleaning connection is blocked from communicating with the fermenting tank,
      the cleaning connections are connectable via lines and the control valves to the circulating pump and the at least one filter such that the at least one cleaning media is circulatable between the cleaning device and the fermenting tank,
      the lines are hose lines, the control valves are hose pinch valves, and the circulating pump is a hose pinch pump, and
      the cleaning controller is configured to manage the cleaning process by controlling addition and removal of the at least one cleaning medium between the cleaning device and the fermenting tank by
      switching the intermediate switch valves to their respective cleaning start positions,
      circulating the at least one cleaning media through the fermenting tank via the cleaning device circulating pump, the at least one filter, at least one of the first and second cleaning connections, and the immersion pipe cleaning connection,
      circulating a neutralizing agent through the fermenting tank via the cleaning device circulating pump, the at least one filter, at least one of the first and second cleaning connections, and the immersion pipe cleaning connection, and
      injecting air through at least one of the first and second cleaning connections such that the fermenting tank is purged through the immersion pipe cleaning connection.

2. The laboratory fermenter according to claim 1, further comprising:
   a first supply pump configured to supply a base solution to the fermenting tank during the cleaning process; and a second cleaning supply pump configured to supply an acid solution to the fermenting tank during the cleaning process.

\* \* \* \* \*